United States Patent
Williams et al.

(10) Patent No.: US 6,214,016 B1
(45) Date of Patent: Apr. 10, 2001

(54) MEDICAL INSTRUMENT POSITIONING DEVICE INTERNAL TO A CATHETER OR LEAD AND METHOD OF USE

(75) Inventors: Terrell M. Williams; Michael Baudino, both of Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/301,958

(22) Filed: Apr. 29, 1999

(51) Int. Cl.$^7$ .................................................. A61F 11/00
(52) U.S. Cl. ................................................. 606/108
(58) Field of Search ..................... 606/108, 110, 606/113, 114, 129, 194, 200, 198; 623/1.11, 1.23

(56) References Cited

U.S. PATENT DOCUMENTS

| | | | |
|---|---|---|---|
| 3,941,119 | * | 3/1976 | Corrales ................................. 600/434 |
| 4,323,071 | * | 4/1982 | Simpson et al. ...................... 606/194 |
| 4,555,243 | * | 11/1985 | Markham ............................... 604/263 |
| 4,873,983 | | 10/1989 | Winters . |
| 4,917,102 | | 4/1990 | Miller et al. . |
| 4,981,482 | * | 1/1991 | Ichikawa ............................... 606/108 |
| 5,026,377 | * | 6/1991 | Burton et al. .......................... 606/108 |
| 5,143,067 | | 9/1992 | Rise et al. . |
| 5,195,968 | | 3/1993 | Lundquist et al. . |
| 5,308,324 | | 5/1994 | Hammerslag et al. . |
| 5,370,675 | | 12/1994 | Edwards et al. . |
| 5,551,426 | | 9/1996 | Hummel et al. . |
| 5,571,168 | * | 11/1996 | Toro ....................................... 606/108 |
| 5,601,591 | * | 2/1997 | Edwards et al. ...................... 606/108 |
| 5,792,110 | | 8/1998 | Cunningham . |
| 5,865,843 | | 2/1999 | Baudino . |
| 5,876,408 | * | 3/1999 | Alt et al. ............................... 606/129 |

OTHER PUBLICATIONS

Georges Schaltenbrand and A. Earl Walker, "Stereotaxy of the Human Brain", 1982.

T.W. Duerig, A.R. Pelton, and D. Stockel, "The Use of Superelasticity in Medicine".

* cited by examiner

*Primary Examiner*—Gene Mancene
*Assistant Examiner*—Eduardo C. Robert
(74) *Attorney, Agent, or Firm*—Banner & Witcoff, Ltd.

(57) ABSTRACT

A medical positioning device internal to a catheter or lead for the nonlinear insertion of a catheter or lead into an interior organ. The medical positioning device comprising an outer tubular member, a superelastic inner tubular member having a curvature positioned within the outer tubular member, and an innermost member positioned within the inner tubular member. The superelastic inner tubular member straightens when placed substantially within the outer tubular member and the inner tubular member resumes its original curvature and moves along a curvilinear trajectory when advanced outwardly from the outer tubular member. Insertion of the outer tubular member into the body, advancement of the inner tubular member into an interior organ, and advancement of the innermost member guides and positions a catheter or lead into an interior organ and to a treatment site along a nonlinear insertion path.

14 Claims, 5 Drawing Sheets

MEDICAL INSTRUMENT POSITIONING DEVICE INTERNAL TO A CATHETER OR LEAD AND METHOD OF USE

BACKGROUND OF THE INVENTION

1. Field of the Invention

This invention relates to an improved medical positioning device for the precise positioning of a medical treatment instrument into an interior organ. The invention additionally contemplates a related method of using the present invention. The present medical positioning device penetrates selected tissue to precisely position a medical treatment instrument into an interior organ while minimizing trauma to tissue surrounding the treatment site. By minimizing trauma to surrounding tissue, the medical positioning device allows for greater medical benefits while minimizing side effects. This invention is particularly useful for guiding and positioning a catheter or an electrical stimulation lead into the brain along a non-linear insertion path.

2. Description of the Related Art

In many medical procedures, it is necessary to position a catheter or an electrical stimulation lead at a precise location within a patient's body. Often, precise placement of a medical treatment instrument is difficult because of the location of the treatment site in the body. These difficult treatment sites may be nearby critical body organs, nerves, or other components that are at high risk of being damaged while the instrument is moved to the treatment site.

The placement of catheters and leads into the body, and particularly into the brain, has been primarily in a straight, linear manner. To place the catheter or lead straight into the brain, a straight, solid metal wire, called a stylet, is used. For many potential treatment sites, a straight insertion of a catheter using a wire stylet has drawbacks that prevent the optimal placement of a medical treatment instrument. For example, the straight insertion of an instrument into some portions of the brain would pass through other critical brain areas, which control a patient's sensory or bodily functions, thereby possibly causing damage to a patient's speech, hearing, or sight. For other portions of the brain, a linear insertion route would require insertion through other undesirable locations that would cause increased trauma to the patient. Ideally, a surgeon wishes to guide a catheter or lead into the brain while avoiding these critical brain areas. To avoid these critical brain areas, it has been found to be desirable to insert the medical treatment instrument into the brain along a curved or nonlinear path, so as to allow a surgeon to precisely place a catheter or stimulation lead into the brain on an insertion path that avoids damage to critical brain tissue.

A number of prior art positioning devices exist that allow for the non-linear placement of a catheter or lead into the body. For example, U.S. Pat. No. 5,195,968 to Lundquist shows a catheter steering mechanism utilizing a pull wire type guiding system. Pull wire type guiding systems have been used primarily to place a catheter into the heart by way of coronary veins. Also, U.S. Pat. No. 4,873,983 to Winters, U.S. Pat. No. 4,917,102 to Miller et al, and U.S. Pat. No. 5,308,324 to Hammerslag et al, show flexible movable core guide wires. Flexible movable core guide wires have been primarily used to insert a catheter through the coronary arteries.

The placement of medical treatment instruments into interior organs presents an additional challenge that makes prior art positioning devices less suitable for use in solid, soft tissue interior organs, such as the brain. Known prior art devices have been used primarily in open cavities that are hollow or filled only with a liquid such as blood. Because open cavities are essentially hollow, a surgeon may move a medical positioning device from side to side within the hollow cavity without damaging tissue by the device's side to side movement. In a solid interior organ, like the brain, however, side to side movement would cause sensitive tissue to be damaged or even sliced.

If a surgeon used a pull wire guiding system or a movable core guide wire system to insert a catheter or lead into the brain, it would damage or slice brain tissue. Additionally, movable core guide wires may be excessively flexible and not strong enough to be effectively used for inserting a treatment instrument into and through brain tissue. Because of these drawbacks, surgeons have typically not used pull wire guiding systems or movable core guide wire systems for placing medical treatment instruments into the brain. Instead, brain surgeons have generally used straight stylets for the straight, linear insertion of a medical treatment device into the brain. Thus, there is a need for a medical positioning device that will allow for the precise placement of medical treatment devices into soft tissue interior organs along a curved path with minimal or non-existent, critical lateral or slicing movement.

The present invention is an improved medical positioning device which allows the user to precisely position a catheter or lead into the brain following a non-linear or curved insertion path while minimizing or even eliminating unwanted damage to surrounding brain tissue and trauma to a patient.

SUMMARY OF THE INVENTION

The present medical positioning device allows a catheter, a lead, or other medical treatment instrument to be precisely placed into an interior organ along a curved, nonlinear path. The present invention is particularly suitable for use in the brain. The present invention allows a surgeon to guide a catheter or lead to a specific treatment site into an interior organ following a predetermined nonlinear insertion path designed to avoid critical structures within the organ. The present invention additionally allows for the precise placement of a treatment device along a non-linear or curved insertion path with minimal damage to tissue surrounding the targeted treatment site.

In summary, the present positioning device comprises, in combination, a substantially rigid outer tubular member, an elastically deformable inner tubular member having a curvature, and an innermost member. The elastically deformable inner tubular member is placed inside the outer tubular member and is slidably movable within the outer tubular member. Because the inner tubular member is elastically deformable, the curved portion of the inner tubular member temporarily straightens when it is placed substantially inside the outer tubular member. The superelastic property of the inner tubular member allows it to elastically return to its original curvature when it passes outwardly through the outer tubular member and into bodily tissue. The innermost member is placed inside the inner tubular member and is slidably movable within the inner tubular member. Once the three components are assembled, they are placed within a medical treatment device such as a catheter or lead. Alternatively, the medical treatment instrument is placed within the outer tubular member. In this configuration, the superelastic inner tubular member and the innermost member are slidably movable within the medical treatment instrument.

In operation, a surgeon inserts the outer tubular member into the body until it penetrates a selected organ to a predetermined depth near the treatment site. Once the outer tubular member has been inserted to the proper depth, the surgeon fixes the position of the outer tubular member. The surgeon then advances the elastically deformable inner tubular member out the end of the outer tubular member to bring it closer to the treatment site. When exiting the outer tubular member, the inner tubular member elastically resumes its curvature and advances outwardly along a curved path into and through the organ. Once the superelastic inner tubular member has been advanced to its desired location, the surgeon fixes its position. Next, the surgeon advances the innermost member out the end of the inner tubular member until it reaches the treatment site. As each of the three components is inserted into the body, the medical treatment instrument is also advanced. Thus, the advancement of the innermost member brings the treatment instrument to the treatment site. After the surgeon has stabilized the medical treatment device, for example, a catheter or stimulation lead, in the organ, the surgeon retracts the innermost member, the inner tubular member, and outer tubular member from the patient's body.

These and other advantages of the invention will become more apparent from the following detailed description thereof when taken in conjunction with the following drawings and description of the preferred embodiment.

BRIEF DESCRIPTION OF THE DRAWINGS

The preferred embodiments of the invention will be described in relation to the accompanying drawings. In the drawings, the following figures have the following general nature.

DESCRIPTION OF THE PREFERRED EMBODIMENTS

Figures 2, 3:
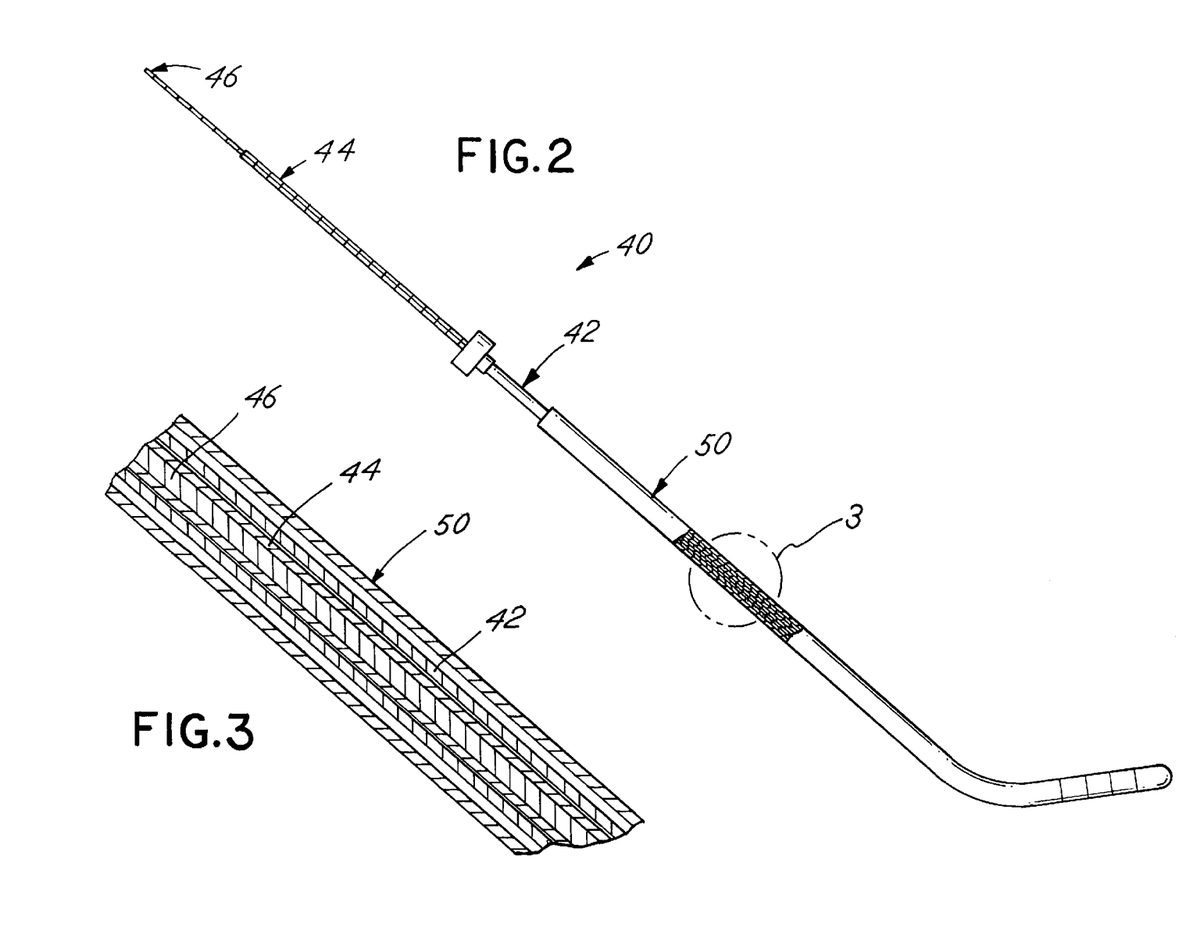
FIG. 2 is a pictorial view of the medical positioning device.
FIG. 3 is an enlarged, broken cross sectional view of the medical positioning device, at View 3 of FIG. 2.

As illustrated in FIG. 2, the medical positioning device embodying the present invention is generally depicted by the numeral 40 and comprises, in combination, an outer tubular member 42, an inner tubular member 44 and an innermost member 46. In the preferred embodiment, the outer tubular member 42, the inner tubular member 44, and the innermost member 46 are internal to a medical treatment instrument 50.

Figure 1:
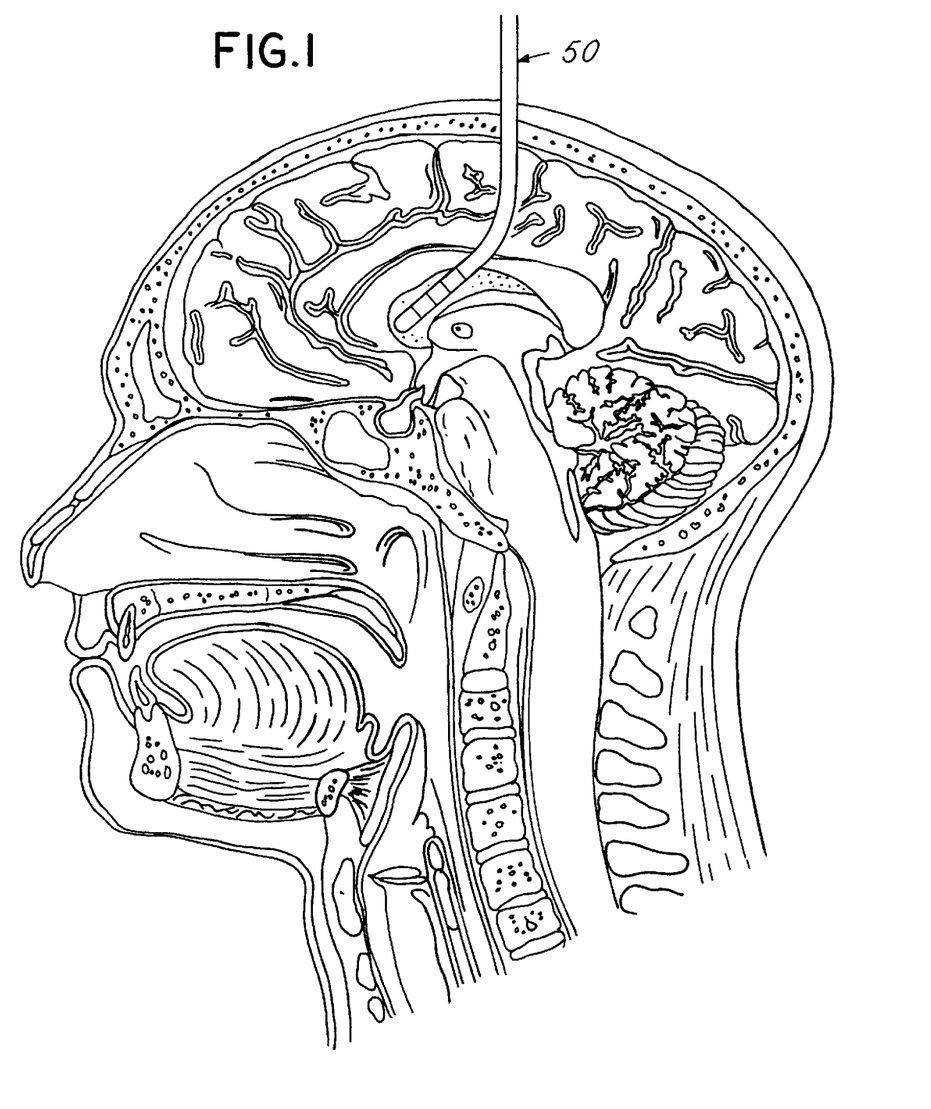
FIG. 1 is a schematic of the brain showing a stimulation lead or catheter inserted into the brain along a non-linear insertion path.

FIG. 1 shows a medical treatment instrument 50 that has been inserted into the brain along a non-linear, or curved insertion path to a position within the brain. In the preferred embodiment, the treatment instrument 50 is a catheter or stimulation lead. One of skill in the art would appreciate that the present medical positioning device may be used with other medical treatment instruments.

Figures 4, 5, 6, 7, 8:
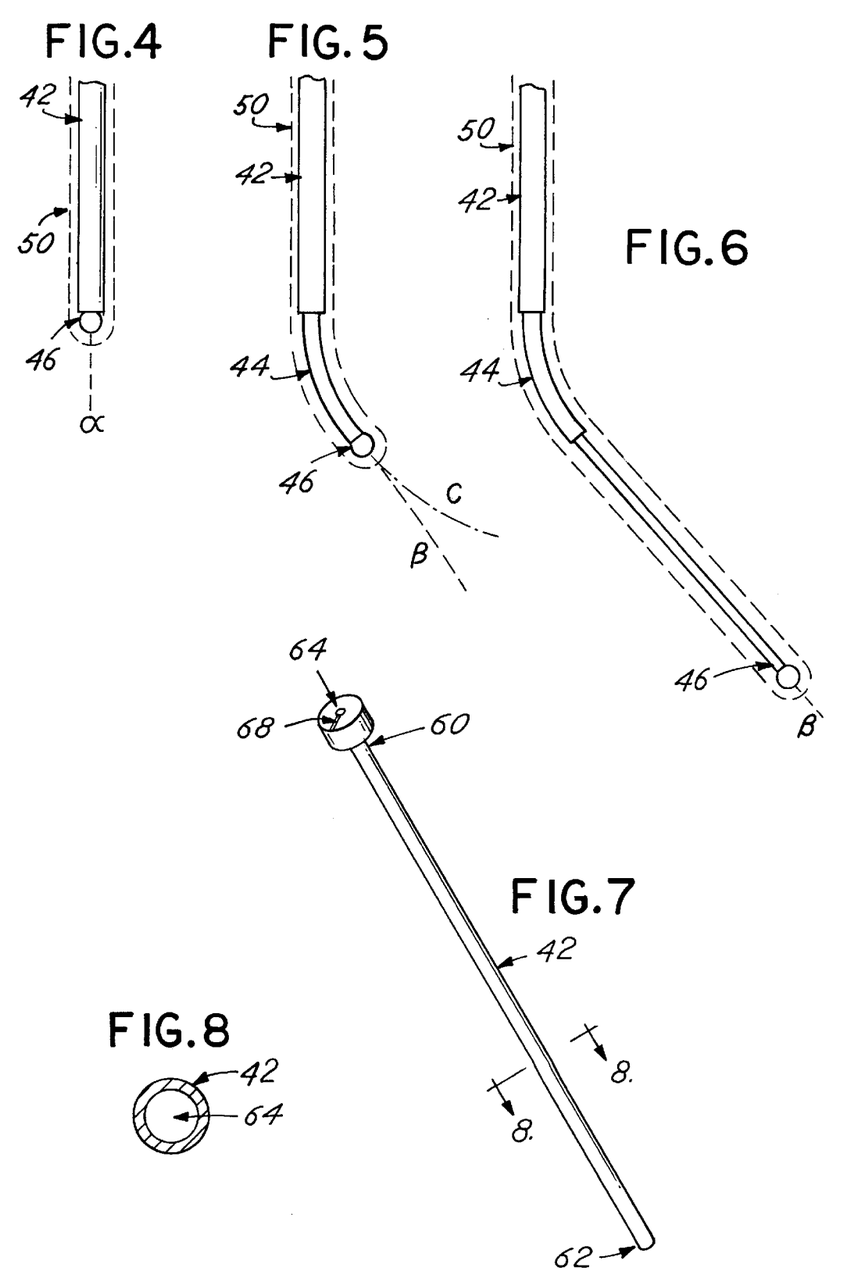
FIG. 4 is an enlarged, truncated pictorial view of the preferred embodiment of the invention of FIGS. 2 and 3 with the outer tubular member advanced in a position of use.
FIG. 5 is an enlarged, truncated pictorial view of the preferred embodiment of the invention of FIGS. 2 and 3 with the outer tubular member and the superelastic inner tubular member advanced to a position of use.
FIG. 6 is an enlarged, truncated pictorial view of the preferred embodiment of the invention of FIGS. 2 and 3 with the outer tubular member, the superelastic inner tubular member, and the innermost member advanced to a position of use.
FIG. 7 is a pictorial view of the outer tubular member in the preferred embodiment of the medical positioning device of FIGS. 2 and 3.
FIG. 8 is a cross sectional view of the outer tubular member taken along line 8—8 shown in FIG. 7.

Referring to FIGS. 7 and 8, the outer tubular member 42 is substantially linear. The outer tubular member 42 has a proximal end 60, a distal end 62, and an axial bore 64 therethrough. Generally, the outer tubular 42 member is substantially linear and rigid to allow its insertion through a surgical opening in the body and into organ tissue. In use, the distal end 62 is inserted into an opening in the body and the proximal end 60 remains outside the body. Preferably, the outer diameter of the outer tubular member 42 is as small as possible to minimize trauma and damage to the tissue of the patient during surgery. Preferably, the outer diameter of the outer tubular member is less than 0.050 inches, more preferably, the outer diameter of the outer tubular member is less than 0.040 inches, and most preferably between 0.030 and 0.040 inches. The outer tubular member should preferably sufficiently long to be able to reach the targeted treatment site. Generally, the outer tubular member will be less than 24 inches long, preferably between 11 and 16 inches long (28–40 cm). As shown in FIG. 8, the outer tubular member 42 preferably has a circular cross sectional shape.

The outer tubular member 42 is typically manufactured from a material which is sufficiently rigid so that it may be inserted through a hole in a patient's body and into an interior organ. Additionally, it should be sufficiently rigid so that at least the outer tubular member's distal portion 62 may be placed in proximity to the selected treatment site. Most preferably, the outer tubular member 42 has a greater rigidity than the inner tubular member 44 such that the outer tubular member 42 remains substantially linear when the inner tubular member 44 is positioned substantially within the outer tubular member 42. The outer tubular member 42 can be manufactured from any inert material which is nontoxic and nonreactive with bodily tissue and that can be formed into substantially linear shapes. For example, materials from which the outer tubular member may be produced include metals such as stainless steel and tungsten.

Figure 9:
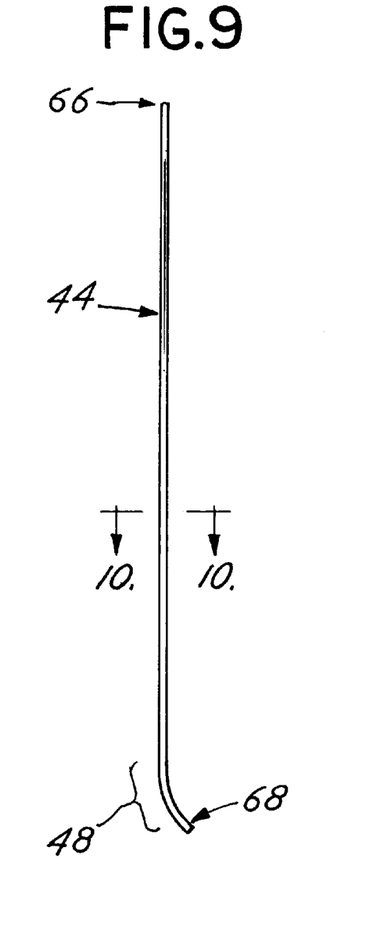
FIG. 9 is a side elevational view of the superelastic inner tubular member in the preferred embodiment of the medical positioning device of FIGS. 2 and 3.
Figure 10:
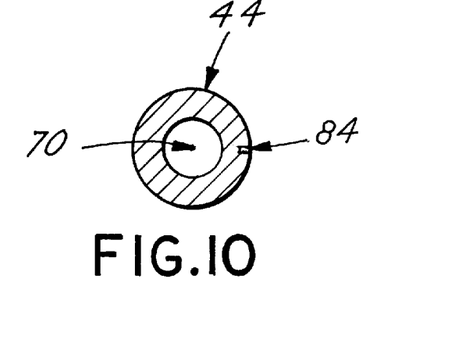
FIG. 10 is an enlarged, cross sectional view of the superelastic inner tubular member taken along the line 10—10 of FIG. 9.

Referring to FIGS. 9 and 10, the inner tubular member 44 has a proximal end 66, a distal end 68, an axial bore therethrough 70 and a curvature 48. In operation, the distal end 68 of the inner tubular member 44 is inserted into the body while the proximal end 66 of the inner tubular member 44 remains outside of the body. Preferably, only the distal end 68 of the inner tubular member 44 has a curvature 48, however, the entire inner tubular member 44 may have a curvature. The invention contemplates providing the surgeon with a series of inner tubular members that cover a range of curvatures. During a surgical planning session, the surgeon will determine which inner tubular member of the series to use during surgery. The amount of curvature will be dependent on the target site within the organ and the surgeon's desired insertion route for the medical treatment device. The typical value for the bend radius of curvature would be between 0.05 and 0.25 inches. The radius of curvature is measured from the devices neutral axis which is the centerline of the device. Larger values are also contemplated. The inner tubular member 44 has an outer diameter which is less than the inner diameter of the outer tubular member 42 so that it may be positioned within the outer tubular member 42. Typically, the outer diameter of the inner tubular member is approximately 0.020 inches. However, a range of diameters between 0.010–0.030 inches are also contemplated for use in the present invention.

In the preferred embodiment, the inner tubular member 44 is fabricated from a superelastic material which allows the inner tubular member to be elastically deformable. The material should be sufficiently elastic such that the inner tubular member 44 is capable of essentially returning to its original curvature 48 upon removal of a force which causes the curvature 48 to temporarily straighten. When the inner tubular member 44 is positioned substantially within the entirety of the linear outer tubular member 42, the inner tubular member 44 temporarily straightens and becomes selectively linear. When the inner tubular member 44 outwardly exits the distal end 62 of the outer tubular member 42, it is sufficiently elastically deformable to allow the inner tubular member 42 to essentially resume its original curvature 48.

In the preferred embodiment, the elastically deformable inner tubular member 44 is manufactured from a Ni—Ti binary alloy having superelastic properties. Many commercial companies manufacture and sell suitable Ni—Ti alloys. For example, Raychem Corp. of Menlo Park, Calif. sells a Ni—Ti alloy under the trade name Tinel® and Nitinol Device & Components of Fremont, Calif. sells a suitable Ni—Ti alloy, SE-508, under the trade name Nitinol. In the preferred embodiment, the binary Ni—Ti alloy has between 48.0 and 52.0 percent atomic weight of Ni, more preferably between 50 and 51 percent, and most preferably between 50.6 and 51.0 percent atomic weight of Ni. Other weight percent ratios are also contemplated for use in this invention. Metals that exhibit superelastic or pseudoelastic properties have the unusual ability to undergo large elastic deformation and also exhibit non-linear unloading behavior. Superelastic metals generally have much greater elasticity, or springback, as compared to stainless steel. Thus, superelasticity allows one to pass a curved instrument through a straight, tubular member and the instrument will elastically return to its curvature once it passes outwardly through the tubular member. Although Ni—Ti binary alloy is the preferred material for the superelastic inner tubular member, one of skill in the art will appreciate that other materials, such as other metals, plastics, polymers, and synthetics, which exhibit similar superelastic properties may be suitable for use in the present invention.

Typically, the entire inner tubular member 44 is fabricated from the superelastic material described above. In an alternative embodiment, the inner tubular member 44 may be manufactured from a combination of materials. For example, the distal portion 68 of the inner tubular member 44 having a curvature 48 may be composed of a elastically deformable material described herein and the proximal portion 66 of the inner tubular member 44 may be composed of a more rigid material such as a metal like stainless steel or tungsten.

Figure 11:
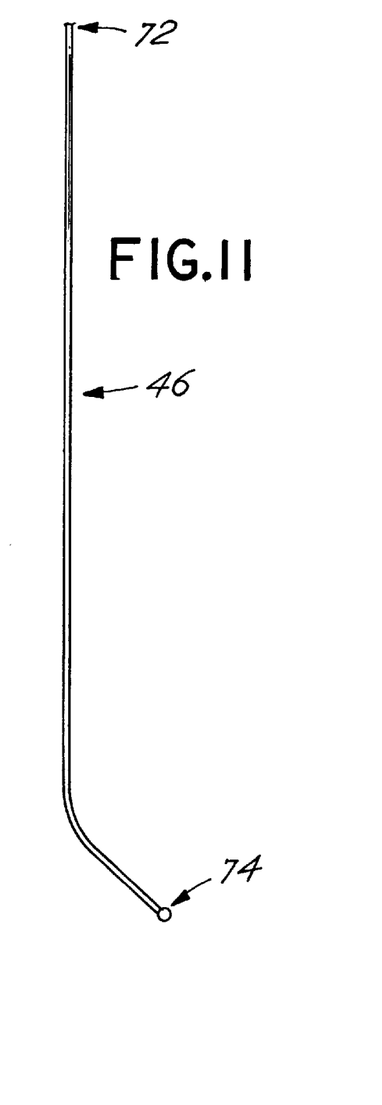
FIG. 11 is a side elevational view of the innermost member, shown bent for assembly representation purposes only, in the preferred embodiment of the medical positioning device of FIGS. 2 and 3.

Referring to FIG. 11, the innermost member 46, or stylet, has a proximal end 72 and a distal end 74. Typically, the innermost member 46 is a straight, solid wire fabricated from a metal such as tungsten or stainless steel. Flat stylets are also contemplated for use. FIG. 11 shows the member 46 bent for representative purposes only. The innermost member 46 should be sufficiently rigid to allow it to penetrate soft bodily tissue, such as brain tissue. Preferably, the distal portion 72 of the innermost member 46 has an outer diameter less than the inner diameter of the inner tubular member 44 so that the innermost member 46 is slidably movable within the inner tubular member 44. Preferably, the distal end 74 of the stylet 46 has a ball or other enlargement that aids in the advancement of the medical treatment instrument 50 to the targeted treatment site. The stylet should be sufficiently long such that the proximal end 72 of the stylet extends beyond the proximal end 66 of the inner tubular member 44 when the stylet is inserted into the body. Typically, the inner tubular member will be approximately 11–16 inches in length.

The innermost tubular member should be dimensioned and fabricated in such a manner that it will freely slide through the curved inner tubular member without kinking. Preferably, the outer diameter of the innermost member 46 is less than 0.020 inches. The outer diameter of the stylet will be dependent on the percent strain recovery of the chosen material, the radius of curvature of the inner member, and the diameter of the inner tubular member. The percent strain of the innermost member is equal to the one half its outer diameter divided by its radius of curvature. For stainless steel, a typical percent strain recovery is approximately 2 percent or less. Typical values for Ni—Ti alloys are in the 6–8 percent range, however, other alloys or materials may have values outside this range. Fabricating the innermost member from a Ni—Ti alloy will allow it to pass through an inner tubular member 44 having a smaller radius of curvature without kinking. For example, in use, a stainless steel stylet having 2 percent recoverable strain could have a radius of curvature typically about 0.25 inches and a diameter of 0.020 inches. Comparatively, a Ni—Ti stylet having 8 percent recoverable strain and an outer diameter of 0.020 inches could have a radius of curvature as small as 0.10 inches.

FIGS. 2–6 and 12 show the spatial relationship of the components comprising the medical positioning device in the preferred embodiment. The inner tubular member 44 is inwardly spaced from the outer tubular member 42. The distal end 68 of the elastically deformable inner tubular member 44 is inserted into the axial bore 64 at the proximal end 60 of the outer tubular member 42. The innermost member 46 is inwardly spaced from the inner tubular member 44. The proximal end 72 of the innermost member 46 is inserted into the axial bore 70 of the outer tubular member 42. In operation, the outer tubular member 42, the inner tubular member 44, and the innermost member 46 are slidably movable within each other and are selectively positionable. These three components are placed internal to a medical treatment instrument 50. When the three components are advanced in a position of use, they form a non-linear structure within an organ that defines a non-linear insertion path for a medical treatment instrument 50. As demonstrated in FIGS. 4–6, these three components are advanced, the medical treatment instrument 50 is guided and precisely positioned into an interior organ along the defined non-linear insertion path.

Figure 13:
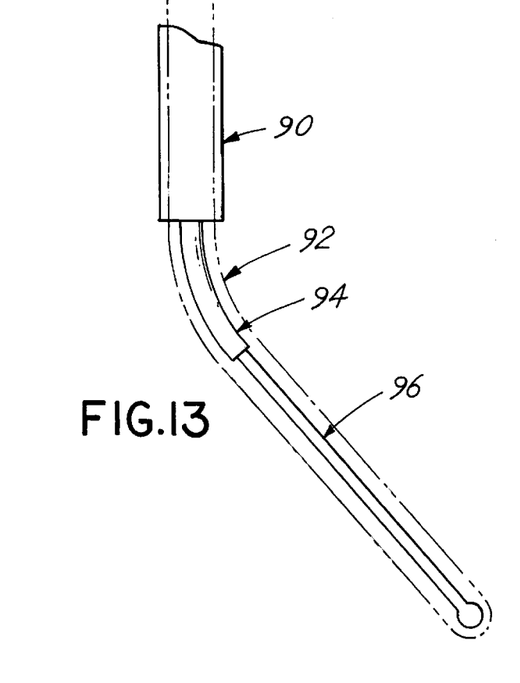
FIG. 13 is an alternate embodiment of the medical positioning device.

An additional configuration of the invention is contemplated and shown in FIG. 13. In this embodiment, a medical treatment device 92 is positioned within an outer tubular member 90. A superelastic inner tubular member 94 having a curvature is positioned within the medical treatment device 92 and is slidably movable therein. An innermost member 96 is positioned within the superelastic inner tubular member 94 and is slidably movable therein. The outer tubular member 90, the inner tubular member 94, and the innermost member 96 will be fabricated from the similar materials and will have similar properties as those in the preferred embodiment previously discussed.

During surgical planning, a surgeon may determine that the linear insertion of a medical treatment instrument into the brain would pass through or damage critical brain areas. The present invention will allow a surgeon to plan and execute the insertion of a medical treatment device into the body via a non-linear insertion trajectory. By using the present medical positioning device, a surgeon may avoid damaging critical structures in the body, and in particular, the brain. Alternatively, the surgeon could access targeted treatment sites from a non-linear trajectory.

There are numerous potential treatment sites within structures in the body, where it is desirable for a surgeon to precisely place a catheter or lead into an organ along a nonlinear path. Although target treatment sites may be reached using a linear insertion path, surgical planning may indicate that the optimal lead or catheter insertion path is nonlinear. In particular, there are numerous sites within the neurological system where the use of this invention may be advantageous. Neurological system is defined broadly in this application to include the brain, the spinal cord, nerves, ganglia, and parts of the receptor organs that receives or interprets stimuli and transmits impulses to the effector organs. Particular sites within the brain where the non-linear placement of a medical treatment device my be desirable include, for example, the subthalamic nucleus (STN), the peduncular pontine nucleus (PPN), the caudate or putamen, the internal and external palladium, the cingulum, the anterior limb of the internal capsule, the anterior nucleus (AN), the centremedian (CM), the dorsal medial nucleus and other nuclei of the thalamus, the hippocampus and other structures in the temporal lobe, the hypothalamus and other structures of the diencephalon, the pons, and the medulla.

For other potential treatment sites, surgical planning may indicate that the optimal placement of catheter or lead is substantially horizontal rather than vertical. The present medical positioning device will allow for a medical treatment device to reach a treatment site along an insertion path that is, in part, an essentially horizontal direction. By selectively advancing the inner tubular member varying the radius of curvature 48 on the inner tubular member 44, the present medical positioning device may allow for the substantially horizontal or lateral placement of the medical treatment device. The present horizontal placement of medical treatment devices may be particularly well suited for placing a medical treatment device into the globus pallidus or striatum of the brain. The present invention may also be well suited for the placement of medical devices near the sacral nerve or the spinal cord. For example, the linear insertion and placement of a stimulation lead would traverse through the foramen and cross the sacral nerve. The present positioning device may be suitable for placing a stimulation lead parallel to the sacral nerve for optimal treatment.

The present invention additionally relates to a method of use. In use, the outer tubular member 42, the inner tubular member 44, and the innermost member 46 are assembled and inserted within a catheter or lead. The selective advancement of the outer tubular member 42, the inner tubular member 44, and the innermost member 46 will guide the catheter or lead to the desired treatment site. FIGS. 4–6 show how the individual components are advanced for the non-linear insertion of the medical treatment instrument 50 into an organ. Once each of the three principal components has been finally advanced, the medical treatment instrument 50 will have been inserted into an organ to the targeted treatment site along a nonlinear path. After the medical instrument 50 has been positioned, the surgeon may treat various ailments and diseases via the medical treatment instrument.

Referring to FIG. 4, the surgeon inserts the substantially linear outer tubular member 42 into the organ being treated, such as a brain. The depth to which the outer tubular member 42 is placed will depend on the location of the site targeted for treatment. The surgeon will determine where to insert the outer tubular member 42 so that it will be positioned near the target site while avoiding critical organ structures. After the outer tubular member 42 is placed to the desired depth and proximate to the targeted treatment site, the surgeon fixes its position. Once fixed, the distal end 60 of the outer tubular member 42 defines a longitudinal axis which further defines a first insertion direction $\alpha$.

Figure 12:
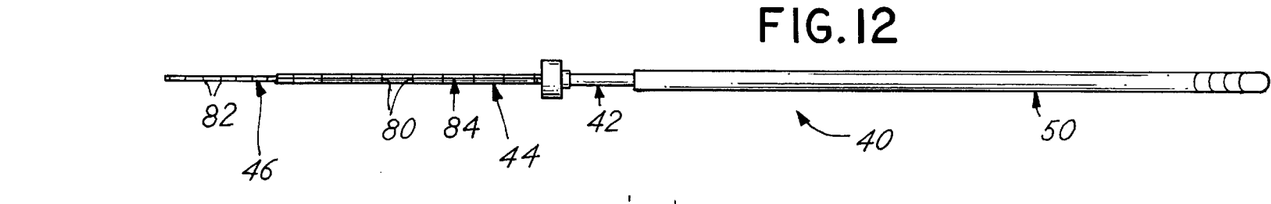
FIG. 12 is a front elevation view of the preferred embodiment of the medical positioning device.

Next, the surgeon selectively advances the inner tubular member 44 out the distal end 62 of the outer tubular member 42 as shown in FIG. 5. In the preferred embodiment, the present invention further comprises an inner tubular member advancement knob. The inner tubular member advancement knob allows the surgeon to precisely advance the inner tubular manner 44. One of skill in the art will appreciate that numerous mechanisms which allow the controlled advancement of tubular parts, such as vernier devices, thumb screws, slides, etc., may be suitable for use with the present medical positioning device. In the preferred embodiment, the outer surface of the inner tubular member 44 will have a plurality of equally spaced apart radial marks 80 as shown in FIG. 12. Preferably, the radial marks 80 are spaced apart in millimeter increments. The radial marks 80 allow the surgeon to visually determine the distance the distal end 68 of the inner tubular member 44 extends beyond the distal end 62 of the outer tubular member 44. The inner tubular member 44 preferably is longer than the outer tubular member 42 and is generally between 8 and 24 inches long, more preferably between 8 and 16 inches in length. The radial marks will additionally allow the surgeon to determine how far into the patient the inner tubular 44 has been inserted.

Because the inner tubular member 44 is fabricated from a superelastic material, it will resume its curvature 48 as it exits the distal end 62 of the outer tubular member 42 and will advance on a known curvilinear trajectory shown by the dashed line (C) in FIG. 5. The curvilinear trajectory (C) the inner tubular member 44 tracks upon exiting from the outer tubular member 42 will be dependent on the curvature 48 of the inner tubular member 44. After choosing the optimal or desired insertion path of the medical treatment instrument to the treatment site, a surgeon will be able to selectively determine the curvature 48 necessary for the medical instrument 50 to advance along the optimal insertion path.

To insure that the inner tubular member 44 exits the outer tubular member 42 in the desired direction, the outer tubular member 42 and inner tubular member 44 have corresponding alignment marks that may be visually aligned. When the marks are in alignment, the inner tubular member 44 will exit the outer tubular member 42 in the predetermined direction. FIG. 7 shows an outer tubular member 42 having an alignment mark 68 at its proximal end 60. FIG. 12 shows an inner tubular member 44 having an axial alignment mark 84 extending along its longitudinal side.

After the surgeon selectively advances the inner tubular member 44 to the desired point along curvilinear trajectory (C), the surgeon fixes the inner tubular member relative to the outer tubular member 42. In the preferred embodiment, a set screw fixes the inner tubular member 44 relative to the outer tubular member 42. After the position of the inner tubular member has been fixed, the distal end 68 of the inner tubular member 44 defines a second insertion direction β which is divergent from the first insertion direction α as shown in FIG. 5. The second insertion direction β is essentially tangent to the curvilinear trajectory (c) of the inner tubular member 44 at its distal end 68. For treatment sites that call for the horizontal placement of a medical instrument, β will be essentially 90 degrees from vertical. After the surgeon advances the inner tubular member to the desired location, the stylet 46 is selectively advanced along the second insertion direction β outwardly from the distal end 68 of the inner tubular member 44 as shown in FIG. 6.

Because the components of the present medical positioning device invention are internal to the medical treatment instrument 50, the surgeon may stabilize the medical instrument 50 prior to removal of the medical positioning device 40. Once the medical treatment instrument 50 has been advanced to its final placement point, the stylet 46 can be withdrawn. Next, the inner tubular member 44 may be withdrawn, followed by the outer tubular member 42. Thus, the catheter or lead has been inserted into the brain along a nonlinear insertion path.

A similar method of use is contemplated for the medical positioning device shown in FIG. 13. For this device, the surgeon inserts the outer tubular member 90 through a surgical opening and brings it near the treatment site. Next, the superelastic inner tubular member 92 is advanced along a curvilinear trajectory into the organ and brought close to the targeted treatment site. Next, the surgeon positions the innermost member 96 to the targeted treatment site. As with the previously discussed method, this method will allow a surgeon to place a medical treatment instrument into the brain along a nonlinear insertion path while avoiding neurological zones within the brain that contain critical brain structures.

The present medical positioning device advantageously allows for the non-linear deployment of a catheter or lead into an interior organ. Advantageously, the present invention allows the surgeon to avoid critical brain structures that a linear insertion of a medical treatment device would hit. The present invention has the additional advantage of having repeatable results because the superelastic inner tubular member will automatically, and repeatably resume its original curvature. Advantageously, the repeatability of the medical positioning device allows for the predictable insertion of the medical instrument to the targeted treatment site. Lastly, the present invention advantageously allows the surgeon to position a medical treatment device into the brain in a controlled manner while avoiding critical neurological zones.

The preferred embodiments of the invention are now described as to enable a person of ordinary skill in the art to make and use the same. Variations of the preferred embodiment are possible without being outside the scope of the present invention. Therefore, to particularly point out and distinctly claim the subject matter regarded as the invention, the following claims conclude the specification.

What is claimed is:

1. A medical positioning device for introducing a medical treatment instrument through a surgical opening in a body and guiding the position of said treatment instrument within interior organs of said body, said medical positioning device comprising, in combination:

an outer tubular member having a proximal end and a distal end, said tubular member being substantially linear;

an inner tubular member slidably movable within said outer tubular member, said inner tubular member having a proximal end and a distal end, said distal end of said inner tubular member having a curvature, said inner tubular member being elastically deformable for allowing said distal end of said inner tubular member to become selectively linear when positioned substantially within the entirety of said linear outer tubular member and to essentially resume said curvature when exiting said distal end of said outer tubular member; and an innermost member slidably movable within said inner tubular member, said innermost member having a proximal end and a distal end, said distal end of said innermost member being movable outwardly from said distal end of said inner tubular member, said outer tubular member, said distal end of said inner tubular member, and said distal end of said innermost member being selectively positionable for defining an interior structure for guiding said treatment instrument to the desired position within a selected interior organ of said body.

2. The medical positioning device of claim 1 wherein said inner tubular member is fabricated from a superelastic material.

3. The medical positioning device of claim 2 wherein said inner tubular member is fabricated from a Ni—Ti binary alloy.

4. The medical positioning device of claim 2 wherein said inner tubular member, said outer tubular member, and said innermost member are concentric relative to each other.

5. The medical positioning device of claim 1 wherein said innermost member is fabricated from a superelastic material.

6. The medical positioning device of claim 5 wherein said innermost member is fabricated from a binary Ni—Ti alloy.

7. The medical positioning device of claim 1 said medical positioning device sized, constructed, and arranged for the medical treatment of the brain.

8. A medical positioning device for introducing a medical treatment instrument through a surgical opening in a body and guiding the position of said treatment instrument within interior organs of said body, said medical positioning device comprising, in combination:

an outer tubular member having a proximal end and a distal end, said tubular member being substantially linear;

a medical treatment instrument slidably movable within said outer tubular member;

an inner tubular member slidably movable within said medical treatment instrument, said inner tubular member having a proximal end and a distal end, said distal end of said inner tubular member having a curvature, said inner tubular member being elastically deformable for allowing said distal end of said inner tubular member to become selectively linear when positioned substantially within the entirety of said linear outer tubular member and to essentially resume said curvature when exiting said distal end of said outer tubular member; and an innermost member slidably moveable within said inner tubular member, said innermost member having a proximal end and a distal end, said distal end of said innermost member being movable outwardly from said distal end of said inner tubular member, said distal end of said inner tubular member and said distal end of said innermost member being selectively positionable for defining an interior structure for guiding said treatment instrument to the desired position within a selected interior organ of said body.

9. The medical positioning device of claim 8 wherein said inner tubular member is fabricated from a superelastic material.

10. The medical positioning device of claim 9 wherein said inner tubular member is fabricated from a binary Ni—Ti alloy.

11. The medical positioning device of claim 8 wherein said innermost member is fabricated from a superelastic material.

12. The medical positioning device of claim 11 wherein said innermost member is fabricated from a binary Ni—Ti alloy.

13. The medical positioning device of claim 8 wherein said medical treatment instrument device is an electrical lead.

14. The medical positioning device of claim 8 wherein said medical treatment instrument device is a catheter.

* * * * *